US00PP36893P2

(12) United States Plant Patent
Clark et al.

(10) Patent No.: US PP36,893 P2
(45) Date of Patent: Aug. 19, 2025

(54) GRAPEVINE PLANT NAMED 'MN 1325'

(50) Latin Name: ***Vitis spp.* hybrid**
Varietal Denomination: MN 1325

(71) Applicant: REGENTS OF THE UNIVERSITY OF MINNESOTA, Minneapolis, MN (US)

(72) Inventors: Matthew Clark, Hopkins, MN (US); James Luby, St. Paul, MN (US); Peter Hemstad, Edina, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 19/025,623

(22) Filed: Jan. 16, 2025

Related U.S. Application Data

(60) Provisional application No. 63/627,783, filed on Jan. 31, 2024.

(51) Int. Cl.
*A01H 6/88* (2018.01)
*A01H 5/08* (2018.01)

(52) U.S. Cl.
USPC ..... Plt./205

(58) Field of Classification Search
USPC ..... Plt./205
CPC ..... A01H 6/88; A01H 5/08
See application file for complete search history.

*Primary Examiner* — Keith O. Robinson
(74) *Attorney, Agent, or Firm* — Penny J. Aguirre

(57) ABSTRACT

The invention is a new and distinct variety of grapevine plant named 'MN 1325' that is characterized by its berries that have a crunchy texture, its berries that have a mild labrusca flavor, its berries that have a thick skin, its berries that are suitable for use in baked goods, similar to a blueberry, and its seedless berries (only seed traces).

2 Drawing Sheets

Botanical classification: *Vitis* spp. hybrid.
Variety denomination: 'MN 1325'.

CROSS REFERENCE TO RELATED APPLICATIONS

This application claims priority to a U.S. Provisional Patent Application, Application No. 63/627,783 filed Jan. 31, 2024 under 35 U.S.C. 119(e), the entire contents of which is incorporated by reference herein.

BACKGROUND OF THE INVENTION

The present invention relates to a new and distinct cultivar of grape plant botanically known as *Vitis* spp. hybrid 'MN 1325', referred to hereafter by its cultivar name, 'MN 1325'. 'MN 1325' is a new cultivar of grape for use as a table grape.

'MN 1325' resulted from an ongoing research program in Excelsior, Minnesota with the objective of the breeding program to develop new cultivars of cold-hardy grapes suitable for table grape production in the Eastern United States.

'MN 1325' originated from a cross made in June of 2007 between the *Vitis* spp. hybrids in the breeding program; the female parent designated as 'MN 1130' (not patented) and the male parent designated as 'MN 1213' (not patented). 'MN 1325' was selected as a single unique plant from the seedlings that derived from the above cross in 2015.

Asexual propagation of the new cultivar was first accomplished by hardwood stem cuttings in February 2018 by the Inventors at a research center in Excelsior, Minnesota. Asexual propagation of the new cultivar by hardwood stem cuttings and tissue culture using meristamic tissue has determined that the characteristics are stable and true to type in successive generations.

SUMMARY OF THE INVENTION

The following traits have been repeatedly observed and represent the characteristics of the new cultivar. These attributes in combination distinguish 'MN 1325' as a new and unique cultivar of *Vitis*.

1. 'MN 1325' exhibits berries that have a crunchy texture.
2. 'MN 1325' exhibits berries that have a mild labrusca flavor.
3. 'MN 1325' exhibits berries that have a thick skin.
4. 'MN 1325' exhibits berries that are suitable for use in baked goods, similar to a blueberry.
5. 'MN 1325' exhibits seedless berries (only seed traces).

The female parent plant of 'MN 1325', differs from 'MN 1325' in having berries that contain seeds. The male parent of 'MN 1325', differs from 'MN 1325' in having berries that are larger in size, red in color, have non-slip skin, and uneven ripening. 'MN 1325' can also be compared to the *Vitis* cultivars 'Louise Swenson' (not patented) and 'Somerset Seedless' (not patented). 'Louise Swenson' is similar to 'MN 1325' in being cold hardy and berries that have a mild labrusca flavor. 'Louise Swenson' differs from 'MN 1325' in having berries that are larger in size, primarily green in color, more slip skin, softer flesh, and seeds and in being used primarily as a wine grape. 'Somerset Seedless' is similar to 'MN 1325' in having berries that are seedless and medium in size. 'Somerset Seedless' differs from 'MN 1325' in having berries that are pink in color, uneven ripening, a different flavor profile, and grape clusters that are smaller in size.

STATEMENT REGARDING PRIOR DISCLOSURES BY THE INVENTORS

The Applicants assert that no publications or advertisements relating to sales, offers for sale, or public distribution occurred more than one year prior to the effective filing date of this application. Any information about the claimed plant would have been obtained from a direct or indirect disclosure from the Inventor. The Applicants claim a prior art exemption under 35 U.S.C. 102(b)(1) for disclosures and/or sales that fall within a one-year grace period prior to the filing date. Disclosures include website listings by University of Wisconsin Fruit Program, HortScience (ASHS), ResearchGate, and Acta Horticulturae.

BRIEF DESCRIPTION OF THE DRAWINGS

The accompanying color photographs illustrate the overall appearance and distinct characteristics of the new grapevine. The photographs were taken of 15-year-old plants of 'MN 1325' as grown under standard field conditions in Excelsior, Minnesota.

The photograph in FIG. 1 provides a view of the plant habit of 'MN 1325' with fruit.

Figure 1:
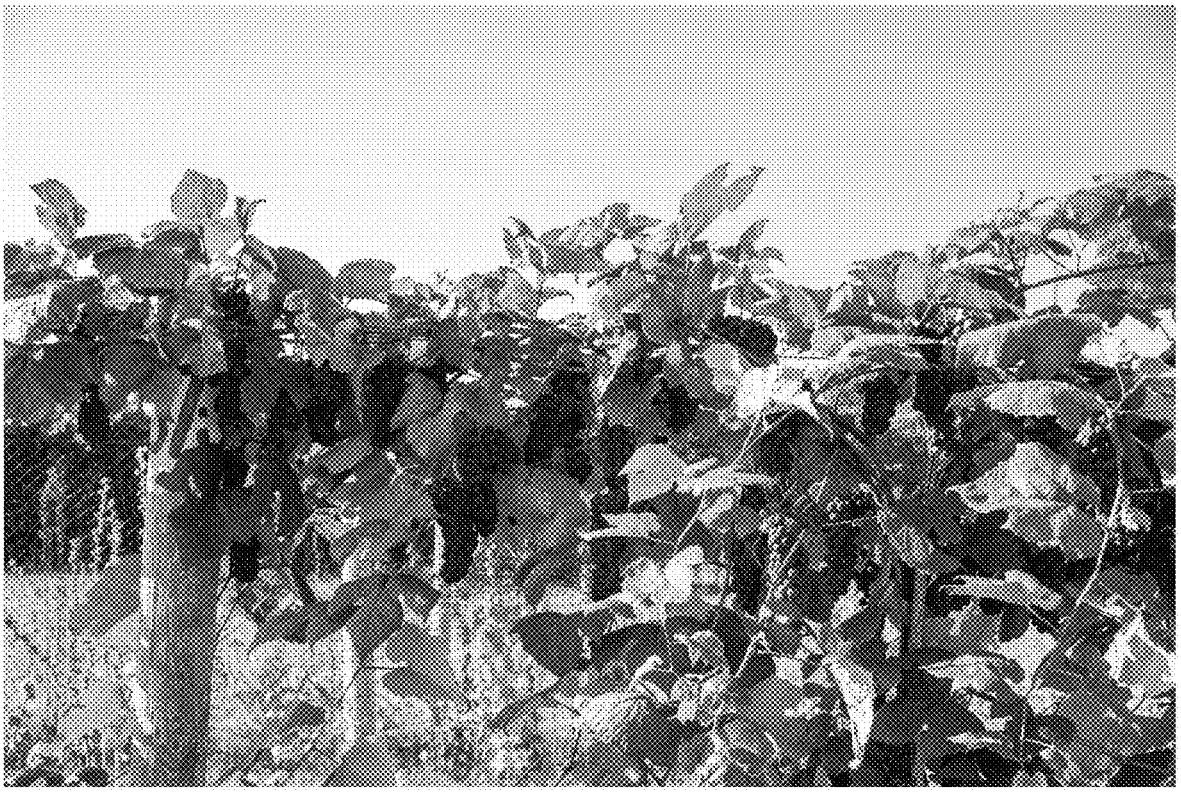
Figure 2:
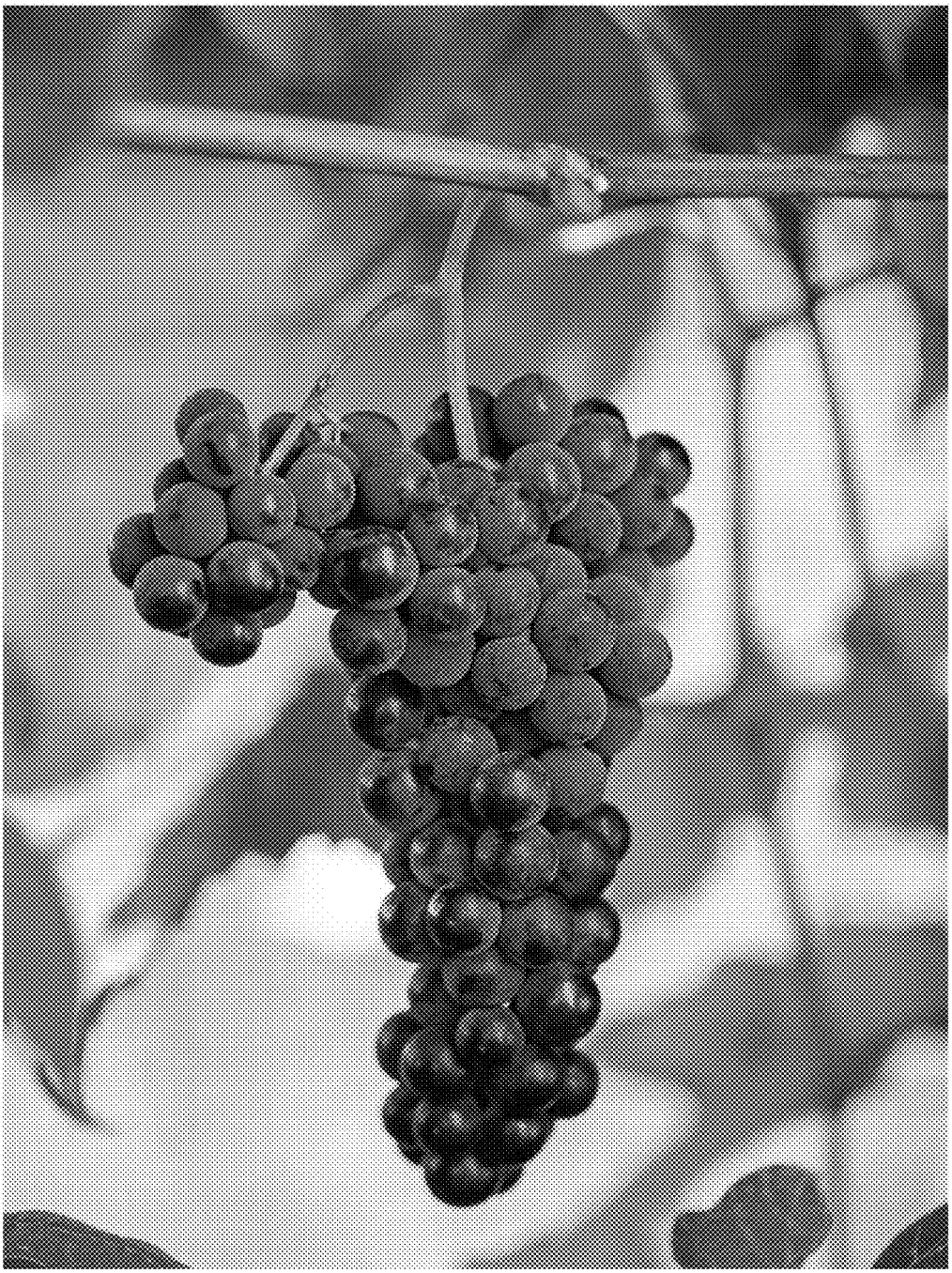

The photograph in FIG. 2 provides a close-up view of a mature cluster of berries of 'MN 1325'.

The photographs depict color features as true as is reasonably possible with the digital photography methods used and the color values cited in the detailed botanical description accurately describe the new *Vitis*.

DETAILED BOTANICAL DESCRIPTION

The following traits have been repeatedly observed and represent the characteristics of the new cultivar. The measurements, observations and descriptions that follow describe a plant 15 years in age as grown outdoors in a trial vineyard in Excelsior, Minnesota. 'MN 1325' has not been observed under all possible environmental conditions and the phenotype may vary somewhat with variations in temperature, day length, light intensity, trellis system, pruning, pest control and other cultural practices without, however, any variance in the genotype. Many of the descriptors are based on those set forth by the International Board for Plant Genetic Resources in collaboration with the Organisation Internationale de la Vigne et du Vin (OIV) and the International Union for the Protection of New Varieties of Plants. All dimensions are given as means. The color determination is in accordance with The 2015 Colour Chart of The Royal Horticultural Society, London, England, except where general color terms of ordinary dictionary significance are used.

General description:

*Blooming period*.—Typically first two weeks of June in Excelsior, Minnesota.

*Plant type*.—Perennial fruit producing vine.

*Plant habit*.—Open and orderly.

*Height and spread*.—2.2 m in height, 2.5 m in spread, trained on high cordon.

*Propagation*.—Hardwood stem cuttings.

*Growth rate*.—Moderate.

*Time required for root development*.—Root initiation 2 to 3 weeks, a young rooted plant is produced within one year from a rooted cutting.

Mature canes:

*Color of canes*.—One-year-old canes; vertical striations of 200B and 164B, new canes; 144A, flushed with 183A.

*Length of canes*.—One-year-old canes; average of 2.5 m (prior to pruning).

*Diameter of canes*.—Ranging between 5 mm to 1 cm.

*Diameter at nodes*.—Average of 3 cm.

*Internode length*.—Average of 10 cm.

*Lenticels*.—Very sparsely covered with lenticels, 183A in color, 0.4 mm in diameter, round in shape.

*Cane cross-section shape*.—Oval to round.

*Surface*.—Glabrous.

*Density of hairs on mature cane*.—Moderate.

*Tendril pattern on shoot*.—2,0,2,0 etc. (two nodes with a tendril followed by one node without).

*Tendrils forked*.—Yes.

*Tendril texture*.—Moderate thickness, glabrous.

*Tendril length*.—Average of 17 cm.

*Tendril color*.—Young and mature shoots; 145A.

*Bud width*.—4 mm.

*Bud length*.—6 mm.

*Bud shape*.—Triangular.

*Bud color*.—145A.

*Bud burst*.—Medium.

Trunk:

*Bark texture*.—Rugose, matte, and exfoliating.

*Bark color*.—Striated, a blend of 198A, 197A, and 202A and 202C.

*Trunk shape*.—Oval.

*Trunk diameter*.—An average of 5 cm on diameter.

Leaves: Descriptors including the designations N1 through N5, relate to "OIV—Code Numbers 065-093" of *Preliminary Minimal Descriptor List for Grapevine Varieties* (Dettweiler E., 1991, Institut fur Rebenzüchtung, Geilweilerhof, Germany).

*Length of blade*.—15 cm.

*Width of blade*.—18 cm.

*Shape of blade*.—Fig-like.

*Number of lobes*.—5.

*Blade margins*.—Incised into lobes with lobes moderately to deeply serrated.

*Length of primary (midrib) vein N1 from the tip of the blade to the petiole sinus*.—11.5 cm.

*Length of petiole compared to length of middle vein (midrib)*.—Middle vein is 3.5 cm longer than length of petiole.

*Length of vein N2 from the tip of the first major lobe of the blade to the petiole sinus*.—9.5 cm.

*Length of vein N3 from the tip of the second major lobe of the blade to the petiole sinus*.—9.5 cm.

*Length of vein N4 from the tip of the third major lobe of the blade to where it joins the vein measured in N3*.—5.5 cm.

*Length of vein N5 from the tip of the first tooth proximal to the petiole sinus to where it joins the vein measured in N4*.—5.5 cm.

*Leaf vein anthocyanin*.—None.

*Density of erect hairs between the leaf veins on lower leaf surface*.—Abundant.

*Length of N2 teeth*.—Up to 1 cm.

*Width of N2 teeth*.—Up to 1.5 cm.

*Length/width ratio of N2 teeth*.—1.2 cm.

*Length of N4 teeth*.—1 cm.

*Width of N4 teeth*.—1.2 cm.

*Length/width ratio of N4 teeth*.—1 cm.

*Shape of teeth*.—Convex.

*Arrangement of petiolar sinus*.—Wide open.

*Shape of petiolar sinus*.—Wide open.

*Shape of base of petiolar sinus*.—Lyre-shaped.

*Depth of petiolar sinus*.—3.5 cm.

*Width of petiolar sinus*.—1.5 cm.

*Petiole.*—8 cm in length, 3 mm in width, 144B in color and suffused with 183A.
*Shape of upper sinuses.*—Urn-shaped.
*Shape of base of upper sinuses.*—Rounded.
*Arrangement of upper sinuses.*—Wide open.
*Glossiness of adaxial and abaxial surface.*—None, matte.
*Pubescence on adaxial surface.*—Young leaves; densely covered with short, soft tangled floccose pubescence, 1 mm in length, 157C in color, mature leaves; moderately covered with long, soft tangled woolly pubescence; 3 mm in length, NN155D in color.
*Pubescence on abaxial surface.*—Young and mature leaves are densely covered with short, soft, floccose pubescence.
*Blistering on adaxial surface.*—None.
*Color of adaxial leaf surface.*—Young leaves; with flocci rubbed off 144A, veins 197B to matching surface color, mature leaves; closest to 144A with a tint of 139A.
*Color of abaxial leaf surface.*—Young leaves; 157A, veins a blend of 146A and 152A, mature leaves; closest to 196A, veins 145A.
*Center lobe size.*—8 cm in length and width.
*Lateral lobe size.*—5 cm in length and 7 cm in width.
*Basal lobe size.*—2.5 cm in length, 3 cm in width.
*Density of foliage.*—Moderate.

Young shoots:
*Form of shoot tip.*—Mainly open.
*Density of prostate hairs on tip.*—Moderately pubescent.
*Anthocyanin coloration of the prostrate hairs on tip.*—Moderate.
*Density of erect hairs on tip.*—Moderately dense.
*Petiole pigmentation.*—145A.
*Shoot attitude.*—Semi-erect.
*Shoot pigmentation* (*internodes and nodes*).—145A, flushed with 183A.

Flowers:
*Fragrance.*—Moderately fragrant.
*Mean time of flowering.*—Second week of June when grown in Excelsior, Minnesota.
*Color of calyx.*—144A.
*Flowering shoot vigor.*—Vigorous.
*Flowering shoot attitude.*—Semi-erect to erect.
*Sepal number.*—5, sepals fused into continuous calyx.
*Calyx shape.*—Ring-shaped.
*Calyx size.*—0.5 mm in length, 2 mm in width.
*Calyx apex.*—Fused to ovary.
*Calyx base.*—Fused to pedicil.
*Nectary.*—1.5 mm in diameter, 0.5 mm in length, 145A in color.
*Calyx surface.*—Glabrous.
*Petals.*—5, fused in calyptra cohering at summit; 1.5 mm in width and 1 mm in depth, reflexed after dehiscence, 144A in color, margins slightly translucent and 155B in color.
*Number of flowers/cluster.*—Average of 110.
*No. of clusters per cane.*—Average of 2.
*Flower buds.*—3 mm in length, 1 mm in width, 144B in color, obovate in shape, glabrous and slightly glossy surface.
*Size of individual entire flower.*—5 mm in length, 1.1 cm in width (to end of stamens).
*Pollen fertility.*—Fertile based on use in controlled crosses.
*Reproductive organs.*—Fully developed stamens and fully developed gynoecium.
*Color of stamen.*—Anther; 15A, fading to 158B, filament; NN155D.
*Stamen number.*—Average of 5.
*Filament length.*—Average of 6 mm.
*Anther.*—1 mm in length and diameter, basifixed.
*Pollen quantitity and color.*—Abundant and 15A in color.
*Pistil.*—1, ovary; 1 mm in length, 1 mm in width at base, urn-shaped, glabrous surface, color 143A, stigma; 1 mm in width, <1 mm in length, N144A in color.
*Pedicel.*—2 mm in length, 0.7 mm in width, 145A in color, surface is glossy and glabrous.
*Peduncle.*—6 mm in length, 2 mm in width, 145A in color, surface is glossy and very sparsely covered with woolly pubescence.
*Position of first flowering and fruiting node.*—Typically node 3.

Fruit:
*Cluster length.*—Average of 15 cm (ranges from 12 to 17.5 cm).
*Cluster shoulders.*—Typically 1.
*Cluster diameter.*—Average of 6.3 cm (ranges from 4.5 to 9 cm).
*Cluster weight.*—113.0 g (ranges from 67.0 to 169.1 g).
*Cluster density.*—Dense to very dense, average of 81 berries per cluster.
*Berry weight.*—1.4 g (ranges from 1.3 to 1.5 g).
*Berry length.*—Average of 1.2 cm.
*Berry diameter at equator.*—Average of 1.4 cm.
*Berry shape.*—Round.
*Berry cross-section.*—Circular.
*Berry, color of skin.*—At maturity; 202A with bloom 202B.
*Berry, color of flesh.*—A blend of 202A and 187A, medium anthyocyanin presence.
*Berry firmness.*—Slightly firm.
*Berry skin thickness.*—Medium.
*Berry skin bloom* (*cuticular wax*).—Low.
*Berry size uniformity.*—Medium.
*Berry, separation from pedicel.*—Medium.
*Berry, presence of seeds.*—Only seed traces, nearly seedless.
*Seed number/berry.*—3.
*Seed length.*—5 mm.
*Seed width.*—2.5 mm.
*Seed length/width ratio.*—2.
*Seed weight.*—0.0071 g (dry) or 0.01 g (fresh).
*Seed color.*—A blend of 200C, 200D, and 167B.

Fruit chemistry and harvest: Values represent the means (with ranges in parentheses) for fruit harvested over three growing seasons 2019-2022.
Harvest date.—September 10 (September 9 to September 11) in Excelsior, Minnesota.
Time of beginning berry ripening.—Second to third week of July in Excelsior, Minnesota.
Soluble solids content.—23.69 degree Brix (20.9 to 27.2).
pH.—2.90 (2.73 to 3.03).
Titratable acidity.—7.98 g/L (3.31 to 12.74).
Berry use.—Table grapes (fresh and frozen food market).

Berry storage.—Clusters were stored in commercial packing (clear plastic, vented polyethylene bags) and place in cardboard boxes lines with a standard microperforated poly liner (1%), absorbent pad (under bags of clusters), and slow release $SO_2$-generating pad containing 73.5% $Na_2S_2O_5$ (on top of clusters), boxes were stored at 2.2 degree Celsius, stored up to 6 weeks with acceptable overall appearance, splitting, and decay and 2-4 weeks before rachis browning was below a consumer threshold.

Vineyard performance: Based on observations compiled over four years (2019-2023).

*Susceptibility to powdery mildew* (*Erysiphe necator*).—Low.

*Susceptibility to downy mildew* (*Plasmopara viticola*).—Low.

*Susceptibility to black rot* (*Guignardia bidwellii*).—Low to none.

*Susceptibility to grey mold* (*Botrytis cinerea*).—None.

*Susceptibility to foliar phylloxera* (*Daktulosphaira vitifoliae*).—None.

*Susceptibility to crown gall* (*Agrobacterium tumefaciens*).—None.

*Susceptibility to phenoxy herbicide drift* (*e.g.*, 2,4-*D*).—Moderate.

*Berry splitting*.—Low.

*Berry shelling*.—Low.

*Vigor level*.—Low to medium.

*Cold hardiness*.—At least in USDA Zone 4.

*Wood ripening*.—Moderate.

It is claimed:

1. A new and distinct variety of grapevine plant named 'MN 1325' as described and illustrated herein.

* * * * *